United States Patent
Stauffer

(10) Patent No.: US 6,822,123 B2
(45) Date of Patent: Nov. 23, 2004

(54) FORMALDEHYDE PROCESS

(76) Inventor: John E. Stauffer, 6 Pecksland Rd., Greenwich, CT (US) 06831

( * ) Notice: Subject to any disclaimer, the term of this patent is extended or adjusted under 35 U.S.C. 154(b) by 0 days.

(21) Appl. No.: 10/405,564

(22) Filed: Apr. 2, 2003

(65) Prior Publication Data

US 2004/0199025 A1 Oct. 7, 2004

(51) Int. Cl.$^7$ ............................................... C07C 45/30
(52) U.S. Cl. ..................... 568/475; 568/490; 568/492; 568/493
(58) Field of Search ................ 568/475, 490, 568/492, 493

(56) References Cited

U.S. PATENT DOCUMENTS 4,383,123 A * 5/1983 Ferris et al. ................ 568/473
4,523,040 A * 6/1985 Olah .......................... 568/671

OTHER PUBLICATIONS

Kirk–Othmer, *Encyclopedia of Chemical Technology*, 4th ed., pp. 935–939, vol. 11.
"Science & Technology Concentrates: Cooler kibosh on chlorinated hydrocarbons," *Chemical & Engineering News*, Jan. 6, 2003, p. 24.

* cited by examiner

*Primary Examiner*—Johann Richter
*Assistant Examiner*—Sikarl A. Witherspoon
(74) *Attorney, Agent, or Firm*—Young & Basile, P.C.

(57) ABSTRACT

A process is provided for the production of formaldehyde from methyl chloride. In the process methyl chloride is oxidized with air over a catalyst to give formaldehyde and hydrogen chloride. In a preferred embodiment of the invention, a mixture of two different catalysts is used, one catalyst to promote the hydrolysis of methyl chloride to methyl alcohol, and the other catalyst to oxidize the methyl alcohol so formed to formaldehyde. The reaction kinetics can be regulated by adjusting the proportion of the two catalysts in the mixture. In this manner, the release of heat from the reaction can be controlled and excessive temperatures in the catalyst mixture can be avoided.

8 Claims, No Drawings

FORMALDEHYDE PROCESS

FIELD OF THE INVENTION

The present invention relates to a process for producing formaldehyde from methyl chloride. A heterogeneous catalyst is used to oxidize methyl chloride with air to produce formaldehyde and hydrogen chloride. When integrated with technology for the manufacture of methyl chloride from methane and hydrogen chloride, the process of the present invention offers an independent source of formaldehyde.

BACKGROUND OF THE INVENTION

Most of the world's commercially produced formaldehyde is manufactured from methanol. Two processes are used to convert methyl alcohol to formaldehyde: one employs a silver catalyst and the other a metal oxide catalyst. A good review of these processes is provided by Kirk-Othmer, *Encyclopedia of Chemical Technology*, 4$^{th}$ ed., Volume 11, pages 935–939.

In the silver catalyst process, methyl alcohol and oxygen are passed through a silver gauze at 600° to 650° C. to produce formaldehyde by two simultaneous reactions, dehydration and oxidation. These reactions tend to balance each other, one being endothermic and the other exothermic. The overall yield, based on methanol, ranges from 88 to 92%.

The metal oxide catalyst process operates at significantly lower temperatures, 300° C. to 400° C., and provides yields between 92 and 95%. The main disadvantage of this process is that an excess of air is required to remove the substantial quantity of heat released by the oxidation reaction. This need results in a large volume of gases that must be treated.

Both commercial processes for the production of formaldehyde depend on methanol as the raw material. This restriction makes the economics of the processes sensitive to fluctuations in methanol pricing. Historically this dependence on methanol has resulted in considerable volatility in manufacturing cost.

SUMMARY OF THE INVENTION

The object of the present invention is to provide a process that overcomes the disadvantages of existing formaldehyde processes. Of primary concern is to free producers from their reliance on a single raw material.

In one particular embodiment of the invention, methyl chloride is oxidized with air over a catalyst to give formaldehyde and hydrogen chloride. After separating the hydrogen chloride from the reaction products, formaldehyde is obtained.

The catalyst used in the reaction to convert methyl chloride to formaldehyde may be of two forms. One type of catalyst consists of particles or pellets of uniform composition. The second type of catalyst is comprised of an intimate mixture of particles or pellets of two distinct compositions.

When a catalyst mix is used, the particles of one composition are designed to promote hydrolysis and the particles of the other composition function as a catalyst for oxidation. The proportion of the two different particles may be varied to control the rate of the reaction. Thus, within a catalyst mixture constituting the catalyst bed of a given reactor, a gradient may be established whereby the proportion of the oxidizing catalyst is greater at the inlet of the reactor than at the exit.

The reaction is carried out at a temperature in the range of approximately 250° C. to approximately 400° C. Close control of the temperature is desired in order to obtain maximum yields of product and to extend the life of the catalyst. The process is operated at essentially atmospheric pressure, but higher pressures up to about 10 bar may be employed to reduce the size of the equipment.

DETAILED DESCRIPTION OF THE PROCESS

In the process of the present invention, methyl chloride ($CH_3Cl$) is oxidized by oxygen ($O_2$) from the air to produce formaldehyde ($CH_2O$) and hydrogen chloride (HCl). A catalyst is required for this reaction to prevent the complete oxidation of methyl chloride to carbon monoxide and carbon dioxide. As a result high yields of formaldehyde are obtainable. The conversion of methyl chloride to formaldehyde by the present invention can be given by the following equation.

$$CH_3Cl + 0.5O_2 \rightarrow CH_2O + HCl \qquad 1.$$

The reaction that is represented by the above equation essentially goes to completion. From thermodynamic data for the Gibbs energies of formation and for enthalpies, equilibrium constants were calculated. At 250° C. log $K_p$ is equal to 16.38 and at 400° C. log $K_p$ equals 13.89. The thermodynamic data also indicate that the reaction is highly exothermic. Under standard conditions, the heat of reaction is 28.44 k cal per mol.

Several conclusions can be reached from the above results. First, complete conversion of the methyl chloride can be achieved in a single pass through a reasonably sized reactor. Second, some means must be provided to remove the substantial amount of heat released by the reaction. The preferred method is to use a shell and tube reactor through which a heat-transfer fluid is circulated.

The success of the process depends primarily on the selection of the catalyst. To understand this requirement, it is helpful to examine the reaction mechanism. The oxidation of methyl chloride to formaldehyde can be considered the result of two reaction steps occurring in series. First, methyl chloride is hydrolyzed with water ($H_2O$) to give methyl alcohol ($CH_3OH$) and hydrogen chloride. Second, the methyl alcohol formed in the first step is oxidized with oxygen to form formaldehyde and water. These two steps can be represented by the following two equations.

$$CH_3Cl + H_2O \rightarrow CH_3OH + HCl \qquad 2.$$

$$CH_3OH + 0.5O_2 \rightarrow CH_2O + H_2O \qquad 3.$$

The above two equations can be combined to give equation 1, which represents the overall reaction.

The water required for the first reaction step is supplied by the water released in the second reaction step. Since these reaction steps occur in intimate contact with each other, the water is always in balance. Some moisture, however, may be required to initiate the series of reactions. This need may be supplied by the humidity of the air used in the process.

Both reactions represented by equations 2 and 3 require catalysts. The first reaction step in which methyl chloride is hydrolyzed to methyl alcohol may be catalyzed by copper chloride, zinc chloride, bismuth chloride or by alumina gel, at a temperature in the range of 280° C. to 350° C. The second reaction step whereby methyl alcohol is oxidized to formaldehyde is catalyzed by an iron-molybdenum oxide catalyst, which may be enhanced with chromium oxide. Other catalysts that have been reported to oxidize methyl alcohol include vanadium pentoxide and copper. The oxidation reaction is carried out at a temperature in the range of 250° C. to 400° C.

The above data suggest one approach to catalyst selection. The catalyst could be designed to have a composition that promotes both hydrolysis and oxidation. Such a catalyst might comprise a copper salt that has been shown to be effective for the hydrolysis of methyl chloride as well as for the oxidation of methyl alcohol.

The other approach is to employ two separate catalysts that are comixed. One catalyst, say alumina gel, would promote hydrolysis and the second catalyst, for example, iron oxide-molybdenum oxide, would promote oxidation. The great advantage of this approach is that the formation of methyl alcohol can be regulated by adjusting the proportion of alumina gel in the catalyst mix. In this manner the release of heat can be better controlled, thereby avoiding excessive temperatures in the catalyst bed.

Catalysts are known to lose their activity over a period of time. Furthermore, they are susceptible to poisoning by certain contaminants. In view of these considerations, the oxidation catalysts that work so well with methyl alcohol could lose their effectiveness when exposed to hydrogen chloride. Therefore alternatives were sought. One such candidate is a lanthanide oxide-based catalyst, which has been reported to be extremely effective in oxidizing chlorinated hydrocarbons at temperatures in the range of 250° C. to 350° C. (*Chemical & Engineering News,* Jan. 6, 2003, page 24).

In summary, the potential advantages of using methyl chloride to produce formaldehyde are overwhelming. An alternative to methanol as a raw material would become available. Investment costs could be reduced and operating efficiencies improved. The impact of these changes on formaldehyde markets would be substantial.

The embodiments of the present invention in which exclusive property or privilege is claimed are defined as follows.

I claim:

1. A process for the production of formaldehyde from methyl chloride comprising the steps of:

reacting methyl chloride with oxygen over a catalyst to give formaldehyde and hydrogen chloride; and separating the hydrogen chloride from the reaction products to obtain formaldehyde.

2. A process according to claim 1 in which the catalyst is comprised of an intimate mixture of particles of two different compositions.

3. A process according to claim 2 in which the particles of the first composition promotes the hydrolysis of methyl chloride to methyl alcohol.

4. A process according to claim 2 in which the particles of the second composition promotes the oxidation of methyl alcohol to formaldehyde.

5. A process according to claim 3 in which the particles that promote hydrolysis are comprised of alumina gel.

6. A process according to claim 4 in which the particles that promote oxidation are comprised of lanthanide oxide.

7. A process according to claim 2 in which the proportion of particles of the two different compositions varies within the catalyst mixture.

8. A process according to claim 1 in which the reaction is carried out at a temperature in the range of approximately 250° C. to approximately 400° C.

* * * * *